(12) United States Patent
Martin et al.

(10) Patent No.: US 6,280,439 B1
(45) Date of Patent: Aug. 28, 2001

(54) ADJUSTABLE POSITION INJECTION TUBING

(75) Inventors: Robert Martin, Pointe Claire; Claudia Lueckge, Pierrefonds; Leonilda Capuano, Montreal; Miriam Lane, Ste-Anne de Bellevue, all of (CA)

(73) Assignee: CryoCath Technologies, Inc., Kirkland (CA)

( * ) Notice: Subject to any disclaimer, the term of this patent is extended or adjusted under 35 U.S.C. 154(b) by 0 days.

(21) Appl. No.: 09/352,021

(22) Filed: Jul. 12, 1999

(51) Int. Cl.[7] .................................................. A61B 18/02
(52) U.S. Cl. .............................. 606/21; 606/23; 606/26; 62/293
(58) Field of Search ............................ 606/20–23, 26; 607/105; 62/293

(56) References Cited

U.S. PATENT DOCUMENTS

| 3,266,492 | 8/1966 | Steinberg ........................ 128/303 |
| 4,207,897 | 6/1980 | Lloyd et al. .................... 128/303.1 |
| 5,078,713 | 1/1992 | Varney ............................ 606/23 |
| 5,108,390 | 4/1992 | Potocky et al. ................ 606/21 |
| 5,423,807 | 6/1995 | Milder ............................ 606/20 |
| 5,716,353 | 2/1998 | Matsuura et al. .............. 606/22 |
| 5,755,690 | 5/1998 | Saab ............................... 604/96 |
| 5,759,182 | 6/1998 | Varney et al. .................. 606/21 |
| 5,800,486 | 9/1998 | Thome et al. .................. 607/105 |
| 5,800,487 | 9/1998 | Mikus et al. ................... 607/105 |
| 5,807,391 | 9/1998 | Wijkamp ........................ 606/23 |
| 5,833,685 | 11/1998 | Tortal et al. ................... 606/23 |
| 5,846,235 | 12/1998 | Pasricha et al. ................ 606/23 |
| 5,868,735 | 2/1999 | Lafontaine ..................... 606/21 |

FOREIGN PATENT DOCUMENTS

| 2094636 | * | 9/1982 | (GB) | .................................... 606/23 |
| 5168646 | * | 7/1993 | (JP) | ..................................... 606/22 |
| 628903 | * | 10/1978 | (SU) | .................................... 606/23 |
| 1153901 | * | 9/1982 | (SU) | .................................... 606/23 |

* cited by examiner

Primary Examiner—Lee S. Cohen
(74) Attorney, Agent, or Firm—Gunster, Yoakley & Stewart, P.A.

(57) ABSTRACT

A cryogenic catheter includes an outer flexible member having a cryogenic fluid path defined by an injection tube disposed in the outer flexible member. The injection tube is slidably disposed within the outer flexible member. A guide member may be provided to support the injection tube within the outer flexible member. A wire is attached to the injection tube at one end and further attached to a spool to provide for take-up of the wire.

8 Claims, 5 Drawing Sheets

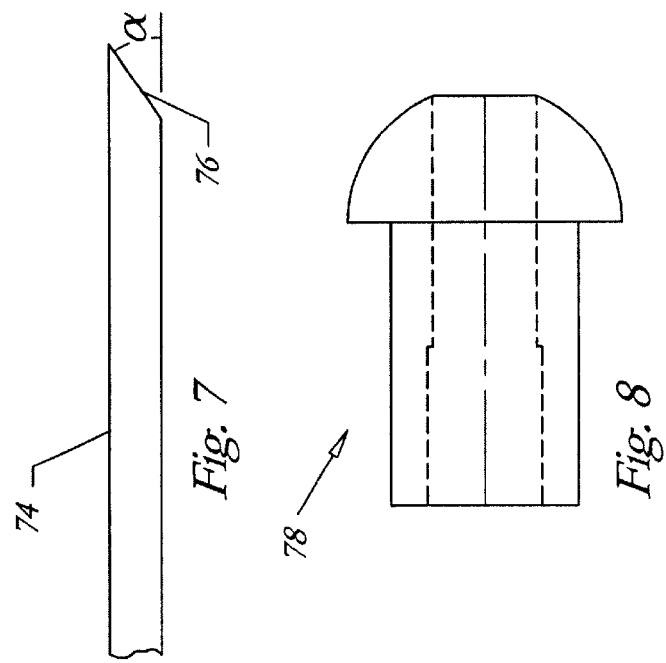
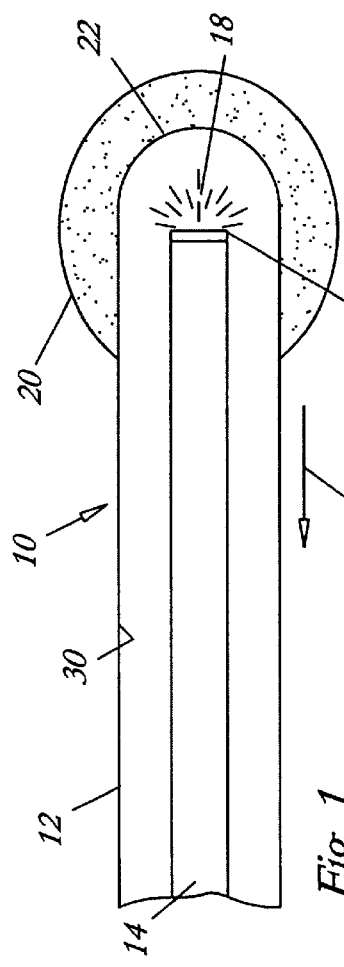
Fig. 1
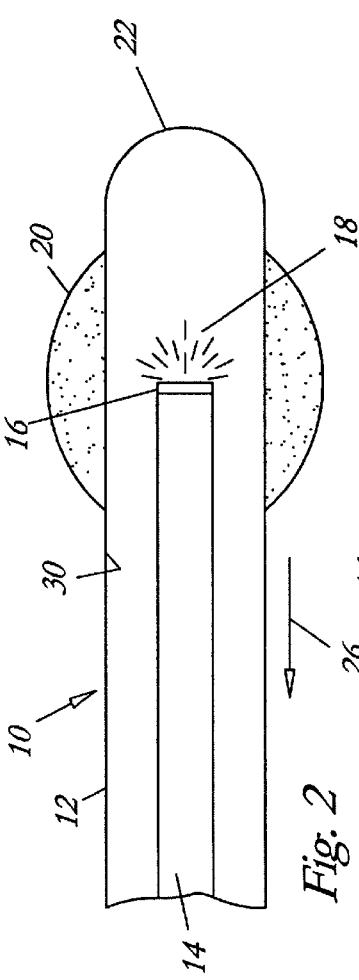
Fig. 2
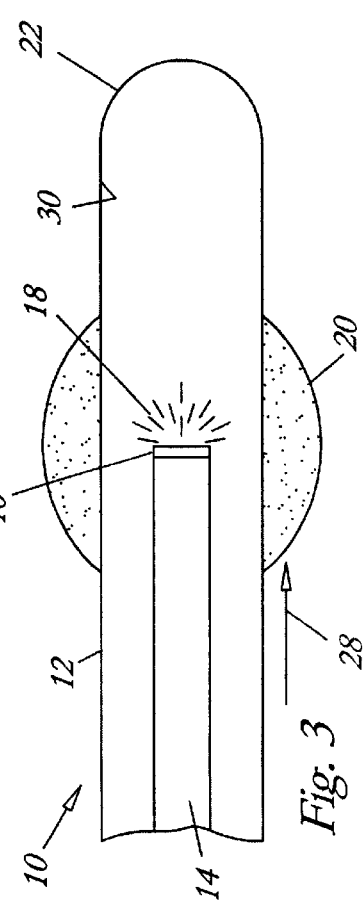
Fig. 3

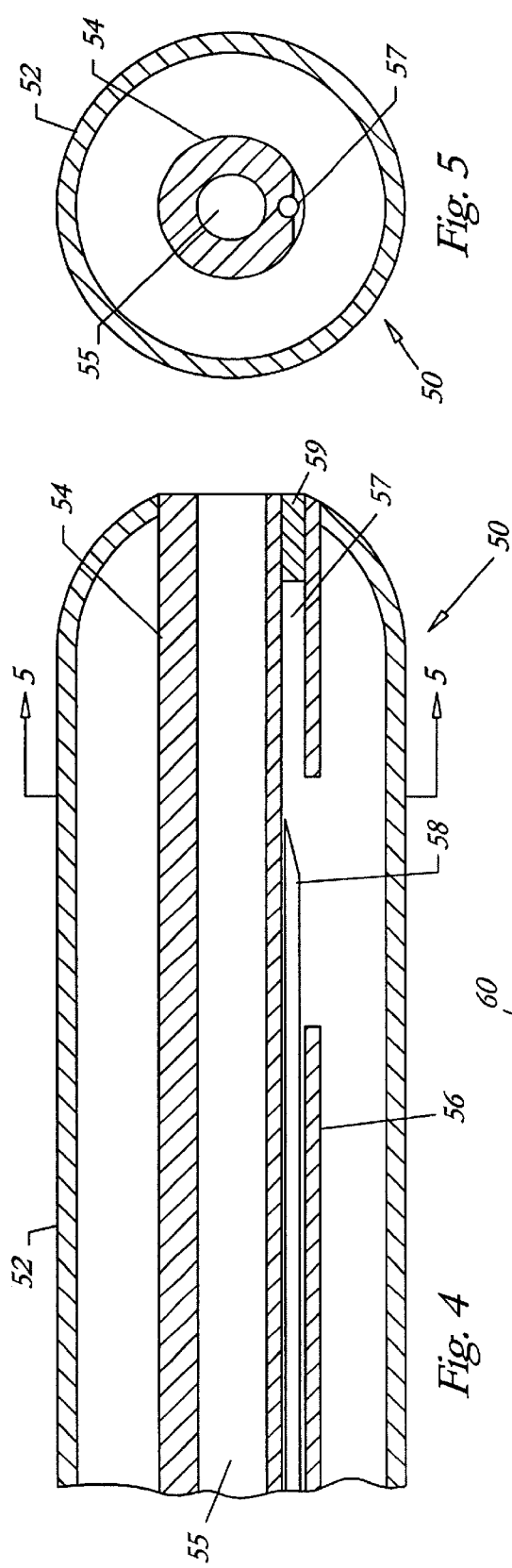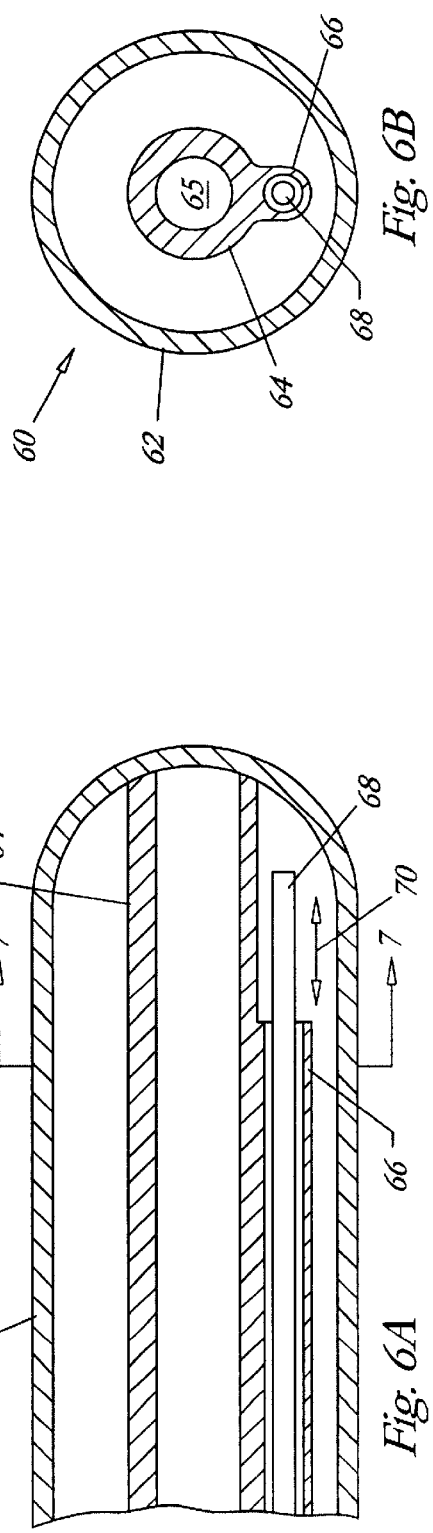

ADJUSTABLE POSITION INJECTION TUBING

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to catheters, and more particularly to a cryosurgical catheter having a slidable injection tube.

BACKGROUND OF THE INVENTION

Medical devices configured for minimally invasive surgery are rapidly becoming the tools of choice for many surgical procedures. Not only do these devices provide an alternative to more invasive surgical tools and procedures, but they have also fostered the development of entirely new procedures.

Devices including highly flexible catheters, as well as rigid and semi-flexible probes have received increased attention in recent years and continue to be refined for cardiovascular, pulmonary, urogenital, and other applications. Devices for each of these applications present different technology and material challenges. Such catheters, for example, can require fluid-tight passages or channels for circulating a cooling fluid (liquid gas) to cool an electrosurgical structure, such as radio frequency ablation electrode, to prevent overheating of the electrode or of surrounding tissue. Similarly, a cooling or cryogenic fluid can be used to reduce the temperature of a structure, such as an ablation surface, to a therapeutic temperature.

Such devices are also useful for procedures involving stenosed arteries and/or blood vessels. As used herein, stenosis means constriction or narrowing. A coronary artery that is constricted or narrowed is thereby referred to as stenosed. These arteries or vessels may be clogged by the buildup over time of fat, cholesterol and other substances.

One procedure for widening coronary arteries is a type of angioplasty, typically a balloon angioplasty. However, many patients undergoing typical angioplasty procedures have renewed narrowing or restenosis of the widened segment within months of the procedure. Restenosed arteries then have to be rewidened.

Restenosis can also occur after a coronary artery bypass graft operation. This type of heart surgery is done to reroute, or "bypass," blood around clogged arteries and improve the supply of blood and oxygen to the heart. In this case, the stenosis may occur in the transplanted blood vessel segments. Like other stenosed arteries, they may have to undergo procedures to reopen them.

Minimally invasive catheters, especially cryogenic based minimally invasive is catheters are well adapted for electrophysiology and restenosis applications. However, the small diameters at which these cryogenic catheters have to be made may result in possible clogging or reduced fluid flow within the device because of the reduced cross sectional areas. The inclusion of guide wires, thermocouple wires, multiple lumens and other features within the cryogenic catheter all also reduce the cross sectional area inside catheter which impedes the space within the catheter that is available for return flow for the fluid within the catheter.

Furthermore, these reduced flows within the catheter makes it difficult to freeze given lengths of the catheter. These limitations may be overcome by forcing cryogenic fluid at relatively high pressures through the catheters. However, such techniques can result in a high pressure differential existing within the catheter. This pressure differential may cause some safety problems since in the case of a component failure, e.g. a leakage, it is desirable to have the tip pressure as low as possible within the catheter. Performance problems may also result since the temperature of the expanding refrigerant is proportional to the ambient pressure at which it expands.

Accordingly, it would be desirable to provide a medical device such as a cryogenic catheter with a slidable injection tube which improves return fluid flow within the catheter and allows given lengths to be frozen without the safety and performance problems of prior art catheters.

SUMMARY OF THE INVENTION

A cryogenic catheter is provided having an elongate outer member and an injection tube slidably disposed within the elongate outer member, where the injection tube defines at least one cryogenic fluid path through the outer member. The injection tube is positionable between a first and second position and at any number of intermediary positions between the first and second position. A guiding sheath may be used to support and guide the injection tube within the outer member.

Movement of the injection tube within the catheter may be provided via a fixed pulley and wire mechanism within the catheter assembly. A spooling mechanism may be integrated within the catheter handle to take up the wire which is attached to the injection tube. The injection tube may also have an end plug attached at one end thereof which is attached directly to the wire. A larger diameter attachment tube or reservoir may also be integrated into one end of the injection tube.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 1 is a schematic illustration of an embodiment of a cryosurgical catheter in accordance with the invention with an injection tube at a first position;

FIG. 2 is a schematic illustration of the catheter of FIG. 1 with the injection tube at an intermediate position;

FIG. 3 is a schematic illustration of the catheter of FIG. 1 with the injection tube at a second position;

FIG. 4 illustrates yet another embodiment of the catheter;

FIG. 5 is a sectional view of the catheter of FIG. 4 taken along line 5—5;

FIG. 6A illustrates yet another embodiment of the catheter;

FIG. 6B is a sectional view of the catheter of FIG. 6A taken along line 6B—6B;

FIG. 7 illustrates another embodiment of an injection tube for use with the catheter of the present invention;

FIG. 8 illustrates an exemplary tip structure for use with the catheter of the present invention;

DETAILED DESCRIPTION OF THE DRAWINGS

Figure 9:
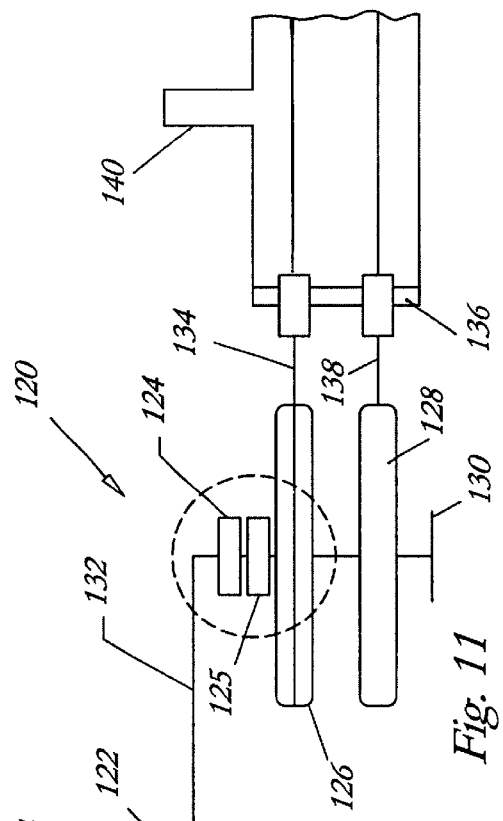
FIG. 9 illustrates another embodiment of the catheter of the present invention.

Referring now to FIG. 1, an exemplary surgical device 10 is illustrated for minimally invasive surgery. In the discussion which follows, "surgical device" is intended to encompass any surgical implement used in association with human or animal medical treatment, diagnosis, study, or analysis. More particularly, a surgical device is intended to encompass any implement or portion thereof that is entirely or partially inserted into a human or animal body by any means of entry, such as through a natural body orifice, an incision, or a puncture. The term surgical device is not intended to connote a limitation to treatment of a single body system, organ, or site. The surgical device can be rigid as a thick steel pipe, completely flexible and pliant like a thread, or have a flexibility between the two extremes. The surgical device can have a diameter that ranges from inches to microns.

Referring now to FIG. 1, the surgical device or catheter 10 includes an elongate outer member 12 having a flexible injection tube 14 disposed within the outer member 12. The injection tube 14 defines a primary fluid path within the outer member 12. A "fluid path" as used herein is intended to encompass an boundary, channel or guide through which a fluid can travel. It can include concentrically disposed catheters, multi lumen catheters, or a single loop of tubing within a sheath.

As used herein, "fluid" is intended to encompass materials in a liquid state, a gas state, or in a transition state between liquid and gas, and liquid and solid. The fluid can be a "cryogenic fluid" capable of reaching or creating extremely cold temperatures well below the freezing point of water; a "cooling fluid" that does not reach or create temperatures below the freezing point of water; a fluid capable of transferring heat away from a relatively warmer structure or body tissue; a fluid capable of transferring heat to a relatively cooler structure or body tissue; a fluid at or capable of creating a temperature between the freezing and boiling points of water; and a fluid at or capable of reaching or creating a temperature above the boiling point of water.

The injection tube 14 of the present invention is adapted for slidable movement to a variety of positions within the outer member 12. In an exemplary embodiment, the injection tube 14 includes at least one opening 16 proximate a distal end of the injection tube. In operation, cryogenic fluid 18 is expelled from the opening 16 and returns to a proximal end of the catheter along a fluid path defined by an inner wall 30 of the outer member 12.

This adjustable positioning of the injection tube 14 allows for greater aggregate cooling power as well as the creation of a variety of different cooling/freeze zones along the length of the outer member 12. As shown in FIG. 1, the injection tube 14 is located at a first position proximate the tip or distal end 22 of the outer member 12. At this first position, the catheter forms an iceball 20 which is located proximate and surrounds the distal end 22 of the outer member 12.

As shown in FIG. 2, the injection tube 14 is slidable in a direction indicated by arrow 24 in FIG. 1 to an intermediary position which is a predetermined distance away from the first position shown in FIG. 1. At this intermediary position, the catheter forms the iceball 20 which now has moved away from the distal end 22 of the outer member 12. The injection tube 14 may then be moved in a direction indicated by arrow 26 to a second position as shown in FIG. 3. In this second position, the ice ball 20 has moved even further away from the distal end 22 of the outer member 12.

Although only first, intermediary and second positions for the injection tube are shown, it is contemplated that the injection tube may be adjustably positionable at any number of intermediary positions between the first and second positions. Furthermore, the injection tube may also be moved back and forth between the first and second positions, such as in the direction indicated by arrow 28 in FIG. 3, depending on the desired cooling pattern. Thus, the flow of cooling fluid along the fluid path through the injection tube can be combined with movement of the injection tube in any number of patterns to provide a desired cooling pattern such as a discontinuous or a continuous ice ball or lesion across the catheter.

Typically, in an exemplary embodiment, the catheter would have a tip between about 2–6 Fr in diameter. It is contemplated that lesions up to 20 cm in length may be frozen using the devices described herein. The cross sectional dimensions of the catheter effectively limits the amount of refrigerant vapor that can be evacuated from the catheter tip region. In one exemplary application, an iceball would be formed at the tip of the catheter and then the injection tube would be slowly pulled back. This movement of the injection tube causes the iceball to also move "backwards" or in a direction towards the proximal end of the catheter. The fluid provided to the injection tube could be shut off at any time to allow the iceball to melt and to re-establish blood flow to the vessel if needed to prevent ischemia in the patient. This construction allows the user to return to treating of the vessel without having to reposition the catheter. This adjustable position injection tube of the present invention is also adaptable for situations where the user would like to freeze, at a given temperature, an area that is larger (longer) than the physical dimensions of the catheter allow.

In an exemplary embodiment, the injection tube may be made out of polyimide but it could be other high strength polymers and it could be metal, such as a stainless steel. As used herein, the term "coaxial" just means that the tubes share a common axis.

Referring to FIG. 4, there is shown yet another embodiment of the present invention. The catheter 50 includes an outer member 52 which has a cantilevered type guiding sheath 54 disposed therein. As shown in FIG. 5, the sheath 54 includes a main guidewire lumen 55 and an injection tube lumen portion 56 which defines an internal lumen 57 which terminates in an end plug 59. An injection tube 58 is slidably disposed within the internal lumen 57 of the injection tube lumen portion 56.

Referring to FIGS. 6A–6B, there is shown yet another embodiment of the present invention. The catheter 60 includes an outer member 62 which has a cantilevered type guiding sheath 64 disposed therein. The sheath 64 includes a main guidewire lumen 65 and an injection tube lumen portion 66. An injection tube 68 is slidably disposed within the injection tube lumen portion 66. However, instead of merely skiving a section of the smaller lumen as in the embodiment discussed above, the entire injection lumen guide would be cut from the dual lumen (guidewire and injection lumen guide) in the tip region of the catheter. In the over the wire application a guidewire lumen will run through the catheter tip. In this embodiment of the present invention this lumen will not run the length of the catheter. In an exemplary embodiment, there will also be at least one thermocouple wire included.

Referring to FIG. 7, an exemplary embodiment of the injection tube is shown. The injection tube 74 is provided with an angled tip 76 which is adapted for directional spraying. The tip may be formed at an angle α in the range of about 20 to 70 degrees and preferably 30 to 45 degrees.

In the embodiment shown in FIGS. 6A–6B, instead of merely skiving a section of the smaller lumen as in the embodiment discussed above, the entire injection lumen guide may be cut from the dual lumen (guidewire and injection lumen guide) in the tip region of the catheter. The tubing is skived so that there is more than 180 degrees of material left for the injection tube to slide within without falling out. In the over the wire application, a guidewire lumen will run through the catheter tip. In this exemplary embodiment, this lumen will not run the length of the catheter. Additionally, there will also be at least one thermocouple wire in this embodiment of the catheter. In the embodiment shown in FIGS. 6A–6B, the guidewire lumen is glued into a catheter tip 78, an embodiment of which is shown in FIG. 8.

In embodiments shown and described herein, thermocouples, not shown, may be disposed along the external surface of the catheter. These thermocouples can be integrated with an internal feedback loop to provide confirmation and independent regulation of the temperature along the region affected by the adjustable injection tubes output.

Referring to FIG. 9, an alternate embodiment of the catheter of the present invention is shown. The catheter 80 includes an outer member 82 which has a rounded tip 84 at one end thereof. The catheter 80 includes an injection tube 86 which is coupled to a plug member 88. The plug member 88 may be glued onto the injection tube 86 or otherwise attached by a friction or interference type fit with the injection tube 86. The plug member 88 is further attached to a wire member 90 which is wound about a pulley member 92. The wire member 90 may be soldered or otherwise similarly fixedly attached to the plug member 88 to avoid unwanted detachment of the wire member 90 from the plug member 88. In an exemplary embodiment, the wire member may be a single strand or a braided type wire sufficient to withstand the forces exerted on the wire in the catheter. Ideally, the wire is of a metallic material and in an exemplary embodiment, has a diameter between about 0.008" to 0.020".

As shown in FIG. 9, the pulley member 92 is positioned proximate the distal end of the catheter 80, preferably near the tip 84. In an exemplary embodiment, the pulley member 92 may be a non-rotating rod member. As shown in FIG. 9, the injection tube 86 may be slidably positioned within the outer member 82 by pulling the wire member 90 in a first direction shown by arrow 94.

Figure 10:
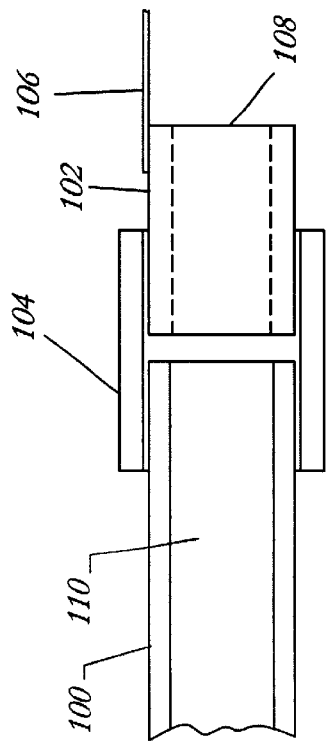
FIG. 10 illustrates another embodiment of the injection tube construction for use with the catheter of the present invention.

Referring to FIG. 10, an alternate embodiment of the injection tube is shown. The injection tube 100 includes a plug member 102 and an attachment tube 104 which are fixedly attached to a distal end of the injection tube 100. The plug member 102 has an internal lumen 108 formed therein which is in communication with the internal lumen 110 of the injection tube 100. Cryogenic fluid expelled from the injection tube 100 may then exit through the plug member 102 through the plug lumen 108. In an exemplary embodiment, the plug member 102 is attached to a wire member 106 which provides for slidable movement of the injection tube in the catheter as described above.

Figure 11:
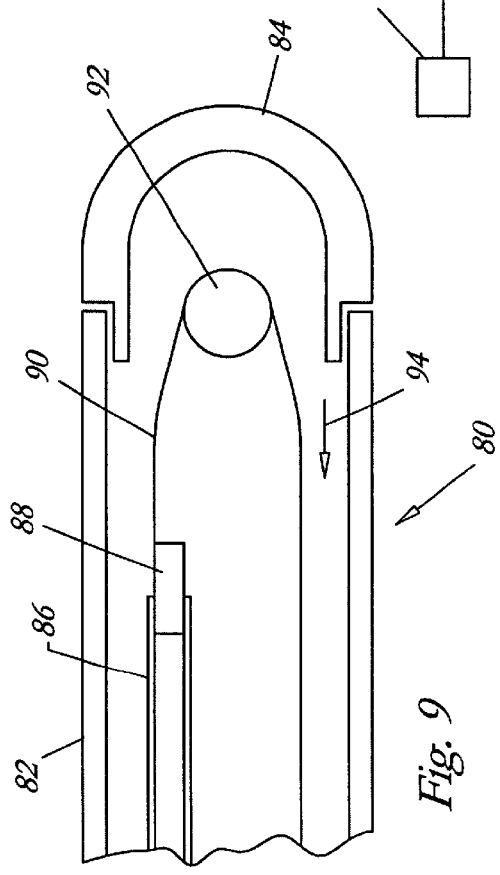
FIG. 11 illustrates a spooling mechanism for use with the catheter of the present invention.

Referring to FIG. 11, a spooling mechanism 120 for providing movement of the injection tube within a catheter is shown. As shown in FIG. 11, in an exemplary embodiment, the spooling mechanism 120 may be disposed within a handle portion, not shown, of the catheter. The spooling mechanism 120 includes an injection port coupling 122, a tube coupling which includes a fixed segment 124 and a rotating segment 125, a first spool 126, a second spool 128 and a spool turning handle 130. The injection port coupling 122 is connected to the tube coupled via a fixed tube 132 which is further connected to the injection tube 134. The injection tube 134 is connected to a wire 138 which provides for slidable movement of the injection tube within the catheter as described later herein. A seal 136 may be provided to prevent leakage of any fluid within the catheter. A vacuum may also be provided via port 140.

Figure 12:
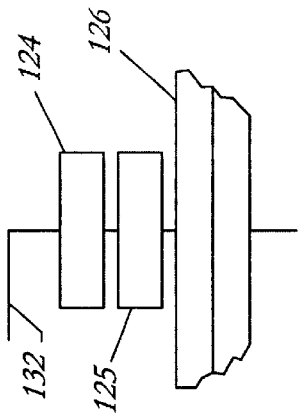
FIG. 12 is a detailed view of portion A of FIG. 11.

A more detailed view of the tube coupling is shown with reference to FIG. 12. In FIG. 12, the fixed tube 132 is connected to the fixed segment 124 of the tube coupling to prevent the fixed tube from twisting thereby adversely affecting the performance of the catheter. The fixed segment 124 is in cooperation with the rotating segment 125 to provide for a connection to the first spool 126 which enables the injection tube within the catheter to be moved back and forth within the catheter.

Figure 13:
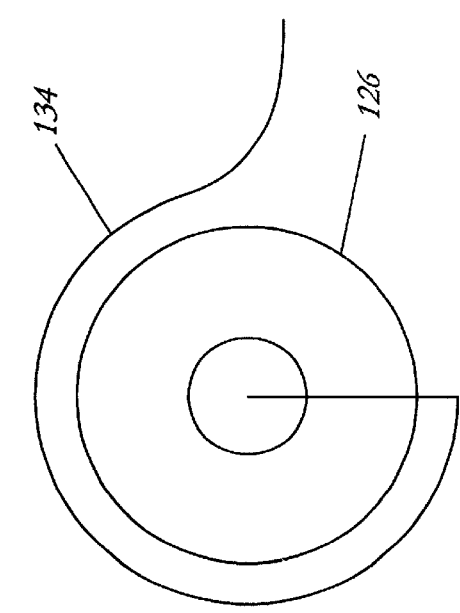
FIG. 13 is a side view of the spool of FIG. 11.

As further shown in FIG. 13, the injection tube 134 winds about the spool 126 to either retract the injection tube when spooled in one direction or to propel the injection forward within the catheter. For example, when rotating the spool turning handle 130 in a clockwise direction, a distal end of the injection tube is brought closer to the tip of the catheter. When rotating the spool turning handle 130 in a counter-clockwise direction, the distal end of the injection tube is pulled away from the tip of the catheter. In other embodiments, these directions may be reversed to form iceball as desired. The spooling mechanism may be rotated back and forth in both directions or solely in one direction as demanded by the application.

Figure 14:
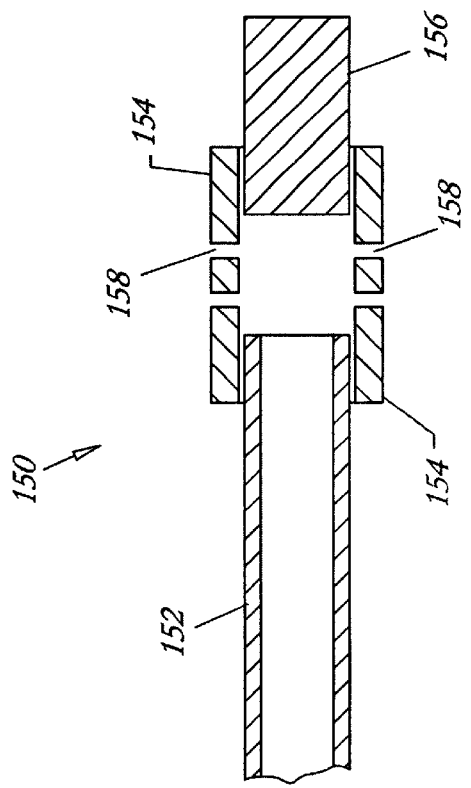
FIG. 14 illustrates yet another embodiment of the injection tube construction for use with the catheter of the present invention.

A further embodiment of a construction of the catheter of the present invention is shown in FIG. 14. As shown in FIG. 14, the catheter 150 includes an injection tube 152 which is coupled to an attachment member 154. At an opposite end of the attachment member 154 is a plug member 156. The attachment member 154 has one or more hole or openings 158 formed thereon. A plurality of openings 158 may be used to create long uniform iceballs along the area to be treated. Preferably, the attachment member 154 has a diameter which is larger than the diameter of the injection tube 152 such that a desirable resistance to flow is created in the catheter via the differential in diameters. The larger attachment tube 154 also allows larger openings 158 to be created in the catheter to achieve desired iceball patterns.

Figure 15:
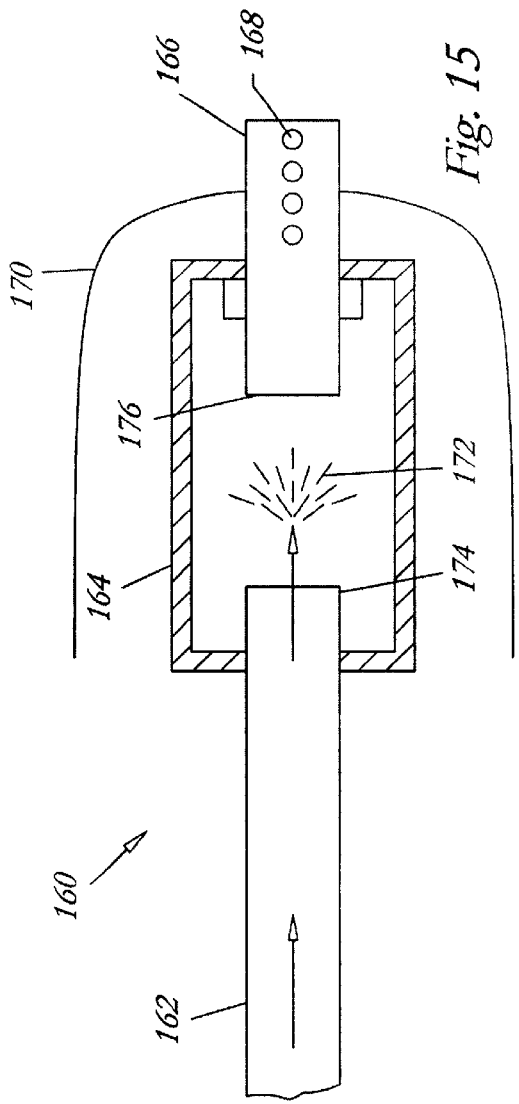
FIG. 15 illustrates still yet another embodiment of the injection tube construction for use with the catheter of the present invention.

Another embodiment of the catheter of the present invention is shown in FIG. 15. The catheter 160 includes an injection tube 162 which is coupled to a reservoir member 164 which has a plug member 166 attached at an opposite end thereof. The plug member 166 has at least one or more openings 168 formed thereon, wherein when cryogenic fluid 172 is expelled from a distal end 174 of the injection tube and into the reservoir member 164, the fluid may exit via the openings 168 in the plug member 166. In an exemplary embodiment, the plug member 166 may have a pull wire 170 attached at a distal end thereof to provide for slidable movement of the injection tube 162 within the catheter. The pull wire may have one or more strands attached to the plug member and in an exemplary embodiment as shown in FIG. 15, the two strands are merged at a proximal end of the catheter. Alternatively, the pull wires may be attached directly to the reservoir member 164 or even the injection tube 162.

In another embodiment shown in FIG. 15, the injection tube 162 is shown fixed within a reservoir member 164. As the fluid pressure is decreased within the catheter, the proximal end 176 of the plug tube member 166 is moved in a first direction towards a distal end 174 of the injection tube 162 and when the pressure inside the reservoir member is increased, the proximal end 176 of the plug tube member 166 is moved in a second direction, away from the proximal end 174 of the injection tube 162. The wires 170 prevent unwanted disengagement of the plug tube member 166. In an exemplary embodiment, the plug tube member 166 has a plurality of openings 168 formed therein.

A discussion of an exemplary operation of the catheter of the present invention now follows. A predetermined amount of refrigerant is introduced into the catheter system which is controlled by pressurization of the liquid refrigerant at a control console. For a given inner diameter injection tube, a given amount of flow will be achieved under a given pressure condition. At the end of the injection tube the refrigerant expands. The temperature of the expanded gas is determined by the ambient pressure at the point of expansion. The region where gas expansion occurs is kept under negative gauge pressure (vacuum) by attaching a vacuum line to the catheter. The pressure differential between the vacuum source (the other end of the vacuum line) and the tip of the catheter (where expansion occurs) is determined by the flow that is occurring and the conditions between the tip of the catheter and the vacuum source (the resistance to the flow).

Because it is desirable to keep the tip of the catheter at a certain temperature, there is a maximum flow level (for a given refrigerant) for a catheter. If flows above that level are obtained, e.g. by forcing more refrigerant down the injection tube, the tip temperature will increase. A given flow rate will provide a set amount of theoretical cooling power (flow rate*heat given up per unit of flow) in the tip region. For example, if trying to cool a cylindrical tip to a certain temperature, the length that can be cooled to that temperature is related to the cooling power available.

Accordingly, the present invention allows cooling of the cylinders without the need to reposition the catheter for the cooling to a given temperature of a longer segment than was previously possible with a fixed injection tube system. Instantaneously, the same length of cooling segment will be cooled as was cooled with a fixed injection tube but by movement of the injection tube, the iceball can be transitioned both forwards and backwards.

Repositioning a shorter tipped catheter will not effectively accomplish the results as described above since in electrophysiology, placement of the tip of the catheter is very critical. For example, when the ice ball is formed, there is adhesion to the heart surface by the iceball. A moving ice ball allows contact to be maintained with the surface of the heart and thus no repositioning of the catheter would be necessary. Repositioning would be required if a shorter catheter was engaged in multiple applications.

In addition, if a catheter with a shorter freezing segment was repositioned, two potential problems could occur, e.g.: 1) If the catheter is not moved far enough a region of the blood vessel will get double dosed; 2) If the catheter is moved too far, a region will not get treated. The moveable injection tube construction eliminates these problems.

An added benefit of the present invention is that a smaller ice ball can be formed. Instead of creating the longest ice ball possible and moving it (or keeping it fixed if it was long enough) a shorter ice ball could be created and moved along the vessel. The smaller ice ball is useful in the coronary arteries where the iceball occludes the vessel. If the patient starts to experience chest pain (ischemic) due to the lack of flow to that region of their heart, the physician will want to cease treatment immediately in order to re-establish blood flow. A shorter ice ball as produced by the catheter of the present invention will also melt quicker thus re-establishing critical blood flow in a shorter amount of time.

It is contemplated that the catheter of the present invention may be used to freeze segments of up to 20 cm long. In an exemplary embodiment, catheter tips will range from about 3 Fr (0.039) in the coronaries to about 5 F (0.065) diameter in the femoral arteries. In an embodiment which forms a linear electrophysiology catheter, the catheter tip would range from about 7 F (0.092) to 9 F (0.118) in diameter. In an electrophysiology catheter embodiment, there would also be a pullwire, at least one thermocouple wire, and at least one EKG wire inside the catheter.

Figure 16:
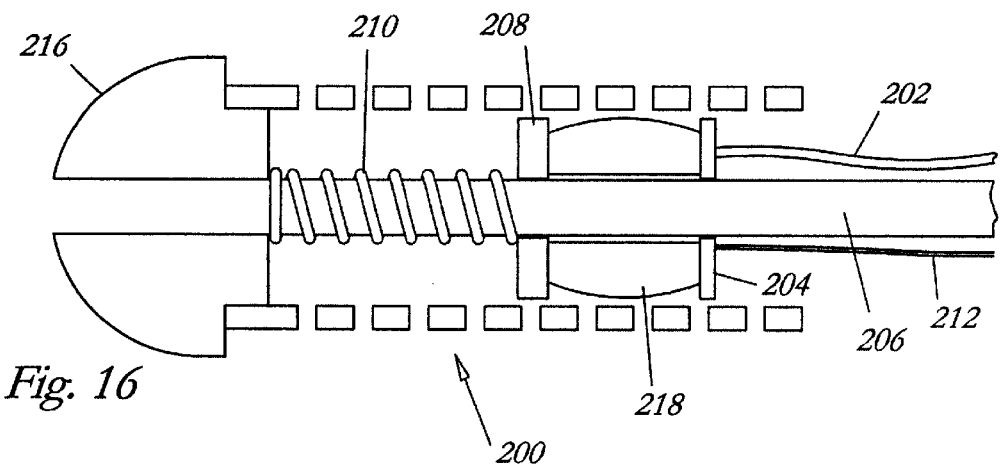
FIG. 16 illustrates another embodiment of the catheter of the present invention.

A further embodiment of present invention is shown in FIG. 16. The catheter 200 includes an injection tube 202 which feeds into a distribute spray system. The catheter includes an underlying tube shuttle member 204, which preferably is teflon lined and creates a shuttle which rides over the outside of a guidewire lumen 206. The shuttle 204 is attached to a disk 208 at one end and at the other end of the disk is attached a nitinol wire 210 shaped in the form of a spring. In an exemplary embodiment, the other end of the nitinol wire 210 is attached to the catheter tip 216. A pull wire 212 is also attached to the shuttle and runs the length of the catheter to the handle, not shown. In an exemplary embodiment, a spray tube 218 may also be attached to the shuttle 204.

Figure 17A:
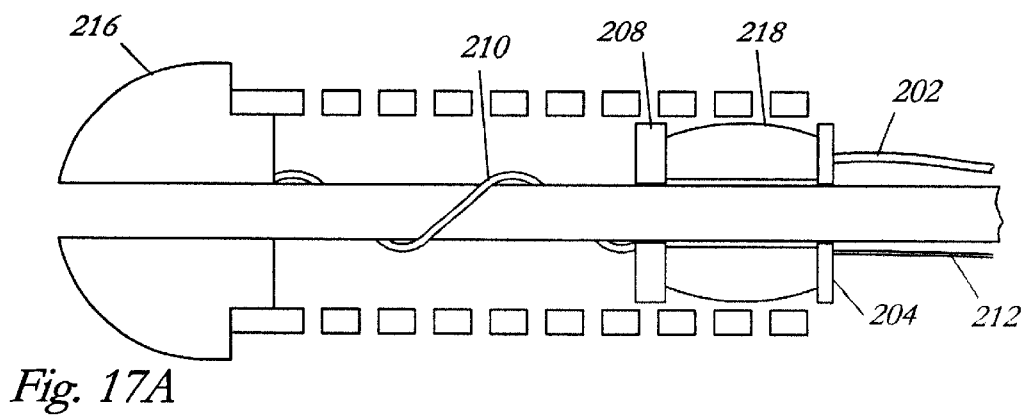
FIG. 17A illustrates the catheter of FIG. 16 in a first configuration.
Figure 17B:
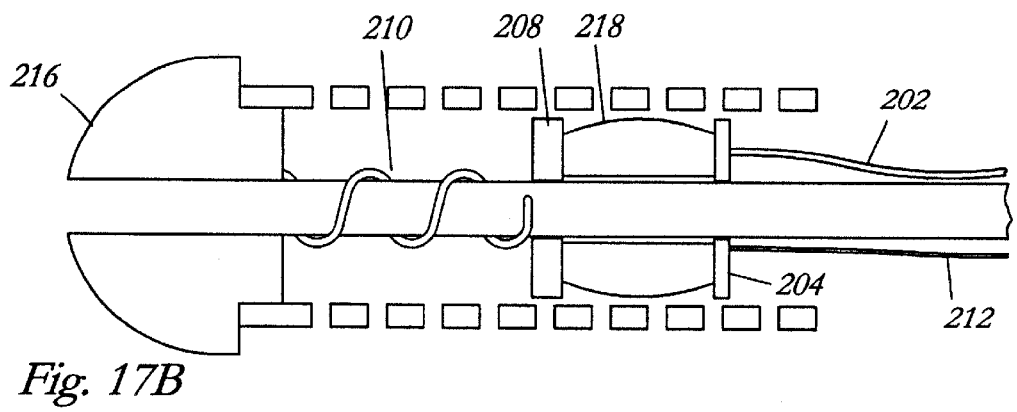
FIG. 17B illustrates the catheter of FIG. 16 in a second configuration.

In an exemplary embodiment, as shown in FIG. 17A, when the catheter begins cooling, the nitinol spring 210 relaxes and the pull wire 212 can be used to move the shuttle 204 longitudinally along the catheter. When the catheter tip 216 warms to body temperature and the pull wire 212 is released, the nitinol wire 210 will take the spring shape again, and it will pull the shuttle forward to the start position, proximal the catheter tip 216, as shown in FIG. 17B.

One skilled in the art will appreciate further features and advantages of the invention based on the above-described embodiments. Accordingly, the invention is not to be limited by what has been particularly shown and described, except as indicated by the appended claims.

What is claimed is:

1. A cryogenic catheter comprising:
   an elongate outer member, and
   an injection tube member having:
      a proximal end portion coupled to a supply of cryogenic fluid, and a distal end portion, the distal end portion further comprising at least one injection orifice formed thereon to selectively release cryogenic fluid, the injection tube member with the at least one injection orifice being movably coupled to the elongate outer member, the injection tube member and the at least one injection orifice being controllably and slidably disposed within the elongate outer member, the injection tube member defining a cryogenic fluid path through the elongate outer member.

2. The cryogenic catheter of claim 1, wherein the injection tube member is longitudinally positionable from a first position to a second position within the elongate outer member.

3. The cryogenic catheter of claim 2, wherein the injection tube member is longitudinally positionable at a predetermined number of intermediary positions between the first position and the second position.

4. The cryogenic catheter of claim 1 where the diameter of the elongate outer member is between about 3 to 5 French and the diameter of the injection tube member is between about 0.004 to 0.015 inches.

5. The cryogenic catheter of claim 1, wherein the catheter allows the creation of a movable iceball.

6. The cryogenic catheter of claim 1, wherein the injection tube has a distal end which is formed at an angle in the range of about 20 to 70 degrees.

7. A method of forming a moveable iceball comprising the steps of:

providing a cryogenic catheter comprising a flexible member having an elongate injection tube disposed therein, the elongate injection tube having a distal end further comprising an injection orifice, and, providing a cryogenic fluid path through the injection tube, distal end, and injection orifice;

introducing a cryogenic fluid into the injection tube wherein the injection tube and injection orifice are each respectively set at a first position within the flexible member; and repositioning the each of the injection tube and injection orifice to a second position within the flexible member.

8. The method of claim 7, wherein the injection tube and injection orifice are each repositioned on at least one intermediary position between the first and second positions.

* * * * *